United States Patent
Park et al.

(10) Patent No.: US 10,722,289 B2
(45) Date of Patent: Jul. 28, 2020

(54) THERMAL ACCELERANT COMPOSITIONS AND METHODS OF USE

(71) Applicants: RHODE ISLAND HOSPITAL, Providence, RI (US); BROWN UNIVERSITY, Providence, RI (US)

(72) Inventors: William Keun Chan Park, Westerly, RI (US); Damian E. Dupuy, Centerville, MA (US); Edward G. Walsh, Danielson, CT (US)

( * ) Notice: Subject to any disclaimer, the term of this patent is extended or adjusted under 35 U.S.C. 154(b) by 537 days.

(21) Appl. No.: 15/389,809

(22) Filed: Dec. 23, 2016

(65) Prior Publication Data
US 2017/0182165 A1 Jun. 29, 2017

Related U.S. Application Data
(60) Provisional application No. 62/381,251, filed on Aug. 30, 2016, provisional application No. 62/387,250, filed on Dec. 23, 2015.

(51) Int. Cl.
*A61B 18/14* (2006.01)
*A61B 18/18* (2006.01)
*A61B 18/00* (2006.01)

(52) U.S. Cl.
CPC .......... *A61B 18/14* (2013.01); *A61B 18/1815* (2013.01); *A61B 2018/00095* (2013.01);
(Continued)

(58) Field of Classification Search
CPC ............... A61B 18/14; A61B 18/1815; A61B 18/00096; A61B 18/00577
See application file for complete search history.

(56) References Cited

U.S. PATENT DOCUMENTS

| | | | | |
|---|---|---|---|---|
| 4,975,246 A | * | 12/1990 | Charm | ..................... A23B 5/01 422/21 |
| 5,057,106 A | | 10/1991 | Kasevich et al. | |

(Continued)

FOREIGN PATENT DOCUMENTS

| | | |
|---|---|---|
| CA | 2319446 C | 9/2010 |
| GB | 2024007 A | 1/1980 |

OTHER PUBLICATIONS

Brace, CL, et al. 2009 Pulmonary thermal ablation: comparison of radiofrequency and microwave devices by using gross pathologic and CT findings in a swine model. Radiology. 251:705-11.
(Continued)

*Primary Examiner* — Michael F Peffley
*Assistant Examiner* — Bo Ouyang
(74) *Attorney, Agent, or Firm* — Nutter McClennen & Fish LLP

(57) ABSTRACT

A thermal accelerant is delivered to a tissue site and localized to modulate the shape, extent or other characteristic of RF or microwave-induced hyperthermic tissue ablation. The accelerant may be provided via an image-guided hand piece or via a lumen added to a microwave antenna, and promotes faster heating, more complete ablation and/or a more extensive treatment region to reduce recurrence of treated cancers, overcoming natural limitations, variations in tissue response and drop-off or thermal loss away from the antenna. The accelerant is delivered as a low-viscosity but heat sensitive fluid, and is fixed in place to provide regions of preferential absorption or heating. Shorter exposure times to heat the far field may allow survival of vulnerable tissue such as vessels, and multiple antennae may be used for effective treatment of irregular or large tumors.

22 Claims, 11 Drawing Sheets

(52) U.S. Cl.
CPC .............. *A61B 2018/00577* (2013.01); *A61B 2018/00982* (2013.01)

(56) References Cited

U.S. PATENT DOCUMENTS

| | | | |
|---|---|---|---|
| 6,340,367 | B1 | 1/2002 | Stinson et al. |
| 6,530,944 | B2 | 3/2003 | West et al. |
| 7,074,175 | B2 | 7/2006 | Handy et al. |
| 8,563,501 | B2 | 10/2013 | Wagner et al. |
| 9,381,157 | B2 | 7/2016 | Santamore et al. |
| 2006/0190063 | A1 | 8/2006 | Kanzius |
| 2007/0135875 | A1* | 6/2007 | Demarais ............... A61F 7/123 607/96 |
| 2007/0135877 | A1* | 6/2007 | Pringle ............... A61B 18/18 607/101 |
| 2011/0034916 | A1 | 2/2011 | Te et al. |
| 2011/0251545 | A1* | 10/2011 | Duffy ............... A61K 31/00 604/21 |
| 2012/0289956 | A1* | 11/2012 | Marc ............... A61B 18/14 606/41 |
| 2014/0056822 | A1 | 2/2014 | Kadushin et al. |
| 2015/0182627 | A1 | 7/2015 | Kim et al. |
| 2015/0265725 | A1* | 9/2015 | Peyman ............... A61B 5/4836 600/2 |
| 2018/0153617 | A1 | 6/2018 | Dupuy et al. |

OTHER PUBLICATIONS

Brace, CL. Evaluation of a thermoprotective gel for hydrodissection during percutaneous microwave ablation: in vivo results. Cardiovasc Intervent Radiol. 2015, 38(3):722-30.

Charpentier, KP. Irreversible Electroporation for the Ablation of Liver Tumors. Are We There Yet? Arch Surg. 2012;147(11)1053-1061.

Chu, KF et al. 2014. Thermal ablation of tumors: biological mechanisms and advances in therapy. Nat. Rev. Cancer 14: 199-208.

Correa-Gallego, C et al. 2014. A Retrospective Comparison of Microwave Ablation vs. Radiofrequency Ablation or Colorectal Cancer Hepatic Metastases. 2014, Ann Surg Oncol. 21(13): 258-264. 4278-83.

Dodd, III, GD et al. Effect of variation of portal venous blood flow on radiofrequency and microwave ablations in a blood-perfused bovine liver model. 2013 Radiology. 267(1): 129-36.

Farrugia, A. Albumin Usage in Clinical Medicine: Tradition or Therapeutic? 2010, Transfusion Medicine Reviews 24(1): 53-63.

Goovaerts, V et al., Molecular Interactions Between Serum Albumin Proteins and Keggin Type Polyoxometalates Studied Using Luminescence Spectroscopy. 2013, Phys. Chem. Chem. Phys., 15, 18378-18387, 2015.

Haefliger, DN. Amphibian albumins as members of the albumin, alpha-fetoprotein, vitamin D- binding protein multigene family. 1989, Journal of Molecular Evolution 29 (4): 344-354.

Keisari, Y et al. Activation of local and systemic anti-tumor immune responses by ablation of solid tumors with intratumoral electrochemical or alpha radiation treatments. 2014. Cancer Immunol. Immunother. 63: 1-9.

Lanuti, M et al. Radiofrequency Ablation for Stage I Non-Small Cell Lung Cancer: Management of Locoregional Recurrence. 2012, Ann Thorac Surg. 93(3): 921-8.

Lichenstein, HS et al. Afamin is a new member of the albumin, alpha-fetoprotein, and vitamin D-binding protein gene family. 1994, The Journal of Biological Chemistry 269 (27): 18149-54.

Lu, DS et al. Radiofrequency Ablation of Hepatocellular Carcinoma: Treatment Success as Defined by Histologic Examination of the Explanted Liver. 2005, Radiology. 234(3):954-60.

Mizukoshi, E et al. Enhancement of tumor-associated antigen-specific T cell responses by radiofrequency ablation of hepatocellular carcinoma. 2013, Hepatology 57: 1448-1457.

Moreland, AJ et al. Evaluation of a thermoprotective gel for hydrodissection during percutaneous microwave ablation: in vivo results. 2015, Cardiovasc Intervent Radiol. 38(3):722-30.

Nelson, SO et al., Factors influencing the dielectric properties of agricultural and food products. 2012, Journal of Microwave Power and Electromagnetic Energy, 46 (2) pp. 93-107.

Ninh, C et al. Photoresponsive hydrogel networks using melanin nanoparticle photothermal sensitizers. 2014 Biomater. Sci., 2, 766-774.

Pethig, R. Dielectric Properties of Biological Materials: Biophysical and Medical Applications. 1984, IEEE Transactions on Electrical Insulation vol. EI-19 No. 5.

Pillai, K et al. Heat sink effect on tumor ablation characteristics as observed in monopolar radiofrequency, bipolar radiofrequency, and microwave, using ex vivo calf liver model. 2015, Medicine (Baltimore) 94(9):e580) 10 pgs.

Schoentgen, F et al. Complete amino acid sequence of human vitamin D- binding protein (group-specific component): evidence of a three-fold internal homology as in serum albumin and α-fetoprotein. 1986, Biochimica et Biophysica Acta (BBA)—Protein Structure and Molecular Enzymology 871 (2): 189-198.

Siddiqui, N et al., A study on viscosity, surface tension and volume flow rate of some edible and medicinal oils. 2013, Int. J Sci, Environ and Tech., 2(6) 1318-1326.

Wang, S. et al, Viscosity-Lowering Effect of Amino Acids and Salts on Highly Concentrated Solutions of Two IgG1 Monoclonal Antibodies. Mol. Pharmaceutics 2015, 12, 4478-87.

Willatt, J et al. Image-guided therapies in the treatment of hepatocellular carcinoma: A multidisciplinary perspective. 2015, World J Hepatol 7(2): 235-244.

International Search Report and Written Opinion of the International Searching Authority in PCT/US16/68517 dated Mar. 29, 2017 (13 pgs.).

* cited by examiner

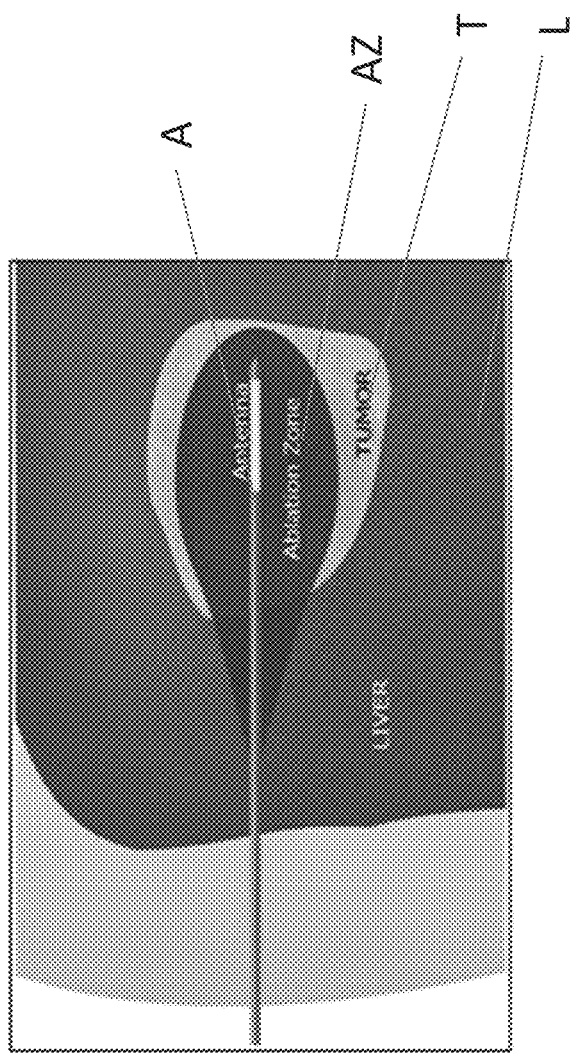
Figure 1A
Figure 1B
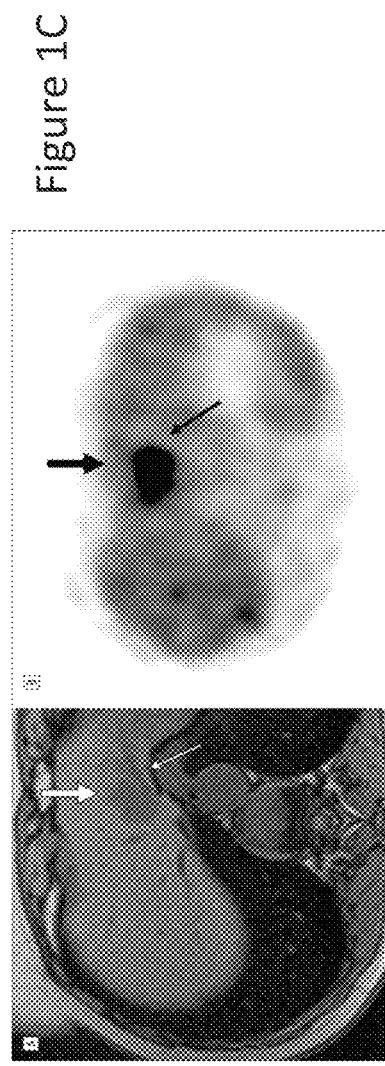
Figure 1C

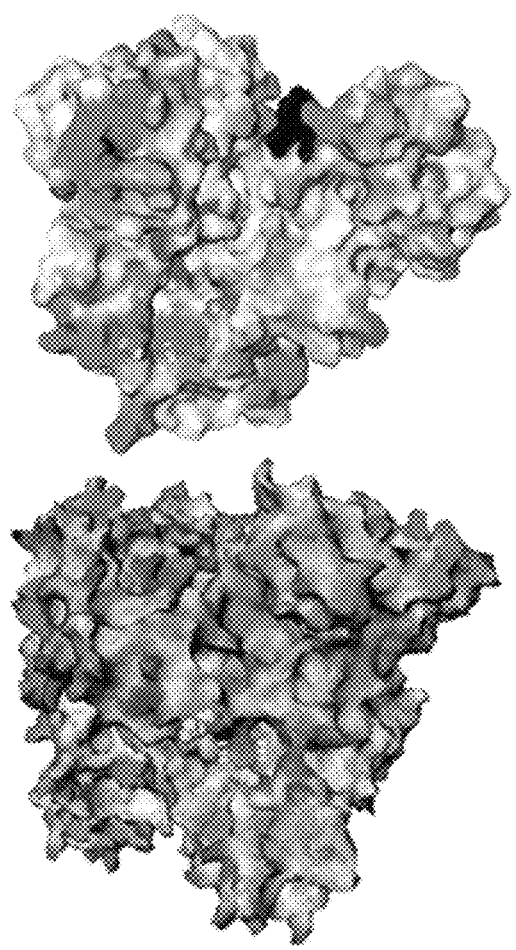
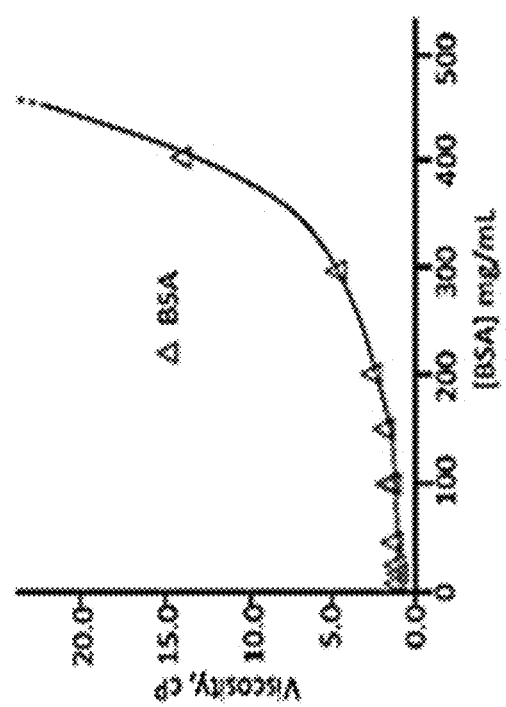
Figure 8A Figure 8B
Figure 9

THERMAL ACCELERANT COMPOSITIONS AND METHODS OF USE

REFERENCE TO RELATED APPLICATIONS

This application is related to, and claims the benefit of Provisional Applications Ser. No. 62/287,350 filed Dec. 23, 2015 and Ser. No. 62/381,252 filed Aug. 30, 2016 in the United States Patent & Trademark Office, both of which are hereby incorporated herein by reference in their entirety including their drawings and appendices.

TECHNICAL FIELD

The present invention relates to methods, materials and equipment for hyperthermal tissue ablation, that is, to the application of energy to heat and destroy tissue such as a tumor located in an internal organ, vessel, bone or other site, without surgery. Among the instruments used for such ablation are monopolar (MP) radiofrequency antennae; bipolar (BP) radiofrequency electrodes; and microwave antennae. These may be inserted transdermally, or via a catheter sheath to access a treatment site, and each has its characteristic action and actuation parameters. The use of such an antenna device for locally heating tissue to achieve hyperthermal tissue ablation may require a characteristic operating duration, applied power level and frequency and type of electromagnetic drive, and the proper selection or setting of these parameters and positioning of the antenna tip will generally depend upon the tissue type as well as the size and shape of the target tumor. Among the different heating modalities, microwave ablation may be applied to internal tissue sites using a needle-like antenna carried in a probe or hand piece, and the active antenna may be imaged, for example by CT imaging, to guide placement precisely in relation to a target tissue site. The target itself may be, or have been, identified by diagnostic imaging, by the same or another medical imaging modality.

Such image-guided microwave tumor ablation has been recognized as a safe, minimally invasive and cost-effective cancer treatment for discrete tumors, and may sometimes be a treatment of choice when other factors render surgery dangerous or otherwise inadvisable.

However, while placement of the microwave antenna may be made anywhere in the body using a simple surgical ablation needle hand piece or commonly available trocar and catheter for placement of the antenna and cable, as appropriate for the intended target site, the effective heating range of a microwave ablation antenna results in an oval- or oblong-shaped ablation region that extends only a relatively small distance around the ablation antenna. Its heating effects may vary, to some extent, depending on the local tissue conditions. While this short effective range will limit unintended damage to most nearby healthy tissue structures, it also presents a drawback, in that microwave ablation drops off rapidly in only a few centimeters, and the ablation may be irregular due to either the rate of microwave heat generation at the site, or heat conduction away from the site into adjacent tissue, or variations in tissue conductivity and dielectric constant (which may be different for each patient). As a result, when treated by microwave hyperthermal ablation, tumors experience a relatively high rate of recurrence (ca. 30%) due to loci of incomplete ablation. The incomplete ablation and consequent tumor cell survival and tumor recurrence may occur because some undetected tumor cells lie outside of the effective ablation zone; because local variations of the tissue characteristics result in intrinsically lower heat generation; because surviving tumor cells are in the vicinity of a blood vessel that acted as a 'heat sink' limiting the temperature rise in a portion of the targeted region during the ablation procedure by increasing thermal conduction away from the intended ablation site; or because the drop-off or shadowing in the far field resulted in great variations of effective temperature around the nominal target temperature.

The effective ablation zone for a microwave needle/antenna is typically an almond-shaped region extending only 2-4 cm from the microwave antenna, as shown in FIG. 1A, which illustrates a microwave needle/antenna A inserted into a tumor T in a patient's liver L such that actuation heats an ablation zone AZ that covers the center, but not the fringes, of the tumor. FIG. 1B shows an actual image of a real-life liver tumor that had metastasized from and presented with a left-side colon cancer. Following resection of the colon primary, the patient was treated with 8 cycles of leucovorin, fluorouracil, and oxaliplatin, as well as bevacizumab (Avastin). The liver tumor, however, was deemed unresectable owing to concerns about functional liver reserve, so it was treated by microwave ablation of tumors in several segments, of which one is indicated by the thick arrow in FIG. 1B. The tumor measured 2.7 cm and abutted the left hepatic vein (thin arrow). Following the ablation procedure a follow-up Positron-emission tomographic scan image was taken. As shown in FIG. 1C, increased fluorodeoxyglucose activity (thick arrow) was observed in a small region, at a location consistent with the presence of residual tumor adjacent to the left hepatic vein (FIG. 1C, thin arrow). Heat sink was implicated as a possible contributing cause of the residual disease. The patient was alive 3 years after initial diagnosis.

Other factors may contribute to sub-optimal ablation efficacy, including incomplete knowledge of the target tissue and its microwave heating characteristics, irregular shape or size of the target, and presence of tissue that limits access or placement of the antenna.

It would therefore be highly desired to provide improved compositions, devices and methods for microwave hyperthermal ablation treatment to address the aforesaid problems of incomplete or irregular ablation, and thereby operate to reduce incidents of tumor recurrence.

It would also be desirable to provide a means to shape, control, enhance or more quickly effect hyperthermal microwave ablation of an intended transdermal target site.

It would also be desirable to provide compositions that mitigate or overcome tissue-dependent temperature variations to enable uniform and effective ablation of diverse tissues and organs.

SUMMARY OF THE INVENTION

These and other desirable goals are achieved in accordance with the present invention by providing a heat substrate composition or thermal accelerant material that is positioned in or near the treatment area and is compounded to efficiently heat up when irradiated. Preferably the substrate can be shaped or otherwise positioned at the target tumor modulate the shape, extent or degree of heating in the intended hyperthermal ablation region of an ablation antenna so as to achieve more complete, better-defined and surgically effective ablation of a tumor site. This will eliminate the problem of incomplete ablation, which currently is the major contributor to recurrence of a tumor, and which currently limits image-guided thermal ablation (IGTA) to a second-line therapy that is best used for tumors under about 3 cm diameter.

The invention will be described by way of examples of heat substrate or thermal accelerant compositions, as well as improved methods of treatment using an image-guided transdermal percutaneous microwave antenna, illustrated below by several thermal accelerant compositions or materials, and methods of positioning the thermal accelerant. Preferred accelerants are formed of a reverse phase polymer, natural or artificial, that may be injected at a defined position as a low-viscosity fluid, and that then forms a gel and remains in place to define, extend, uniformize and/or otherwise enhance local tissue heating. In one embodiment the heat substrate contains a soluble salt, which may operate to enhance microwave absorbance and heating. In another or further embodiment the salt may or condition molecular charge such that the polymer has low viscosity and may be effectively applied as a liquid in and around a tumor or tissue to extend and accelerate heating for hyperthermal ablation using an image-guided transdermal microwave antenna. When microwaved, the composition heats up hotter and quicker than the generally somewhat slower response of tissue, and the thermal accelerant, applied as a low-viscosity fluid may be applied and fixed in various positions to achieve better treatment. Specifically, its faster temperature rise may enable shorter microwave exposure time; it may also increase the rate of thermal rise or the final temperature endpoint for a given treatment duration or position of placement.

The thermal accelerant material may be positioned immediately about the microwave antenna, or may be selectively delivered to a region offset from the antenna, or at the periphery of the tissue target to thereby enhance the completeness of ablation in the far field. The heat substrate may alternatively or additionally be positioned in relation to the tumor and to nearby tissue structures, for example to raise the temperature of tissue between the tumor and a nearby vessel to thereby block thermal conduction away from the intended site (the 'heat sink effect' of circulation in the vessel that would otherwise conduct heat away from the intended ablation region and result sub-optimal heating and ineffective ablation of tumor cells). Thus as a satellite heating body, the thermal accelerant may be positioned, in various procedures, to enhance ablation in the far field, to promote more uniform and complete ablation despite interfering tissue structures, or to selectively increase tissue heating and ablation in a specific site while limiting the necessary near-field exposure ordinarily needed to attain complete ablation.

Examples and representative materials and methods of use in a procedure for microwave tissue ablation are described further below and in the drawings and claims appended hereto. Specific discussions identify suitable synthetic PLGA-PEG-PLGA polymers, as well as formulations based on albumin as reverse phase components of a thermal accelerant for microwave ablation procedures. Certain alkali or alkali earth salts are described as components for tuning the viscosity and/or heating characteristics of the thermal accelerant. See, for example, Appendix A, Appendix B and Appendix C of the priority provisional applications identified supra.

BRIEF DESCRIPTION OF THE FIGURES

These and other features of the invention will be understood from the Figures and Description below, taken together with the Claims appended hereto, wherein FIG. 1A schematically shows non-overlapping ablation and tumor regions of a prior art microwave hepatic tumor ablation treatment;

FIG. 1B shows a metastatic tumor in the liver of a patient and abutting the hepatic vein;

FIG. 1C is a PET scan of that site showing residual tumor growth suggesting that heat sink effect was a contributing cause of the residual disease;

FIGS. 8A and 8B illustrate the surface potential of HSA and of BSA, respectively, with areas of positive and negative charge shaded or colored differently;

FIG. 9 shows the viscosity of BSA as a function of its concentration in mg/mL;

DETAILED DESCRIPTION

Figure 2A:
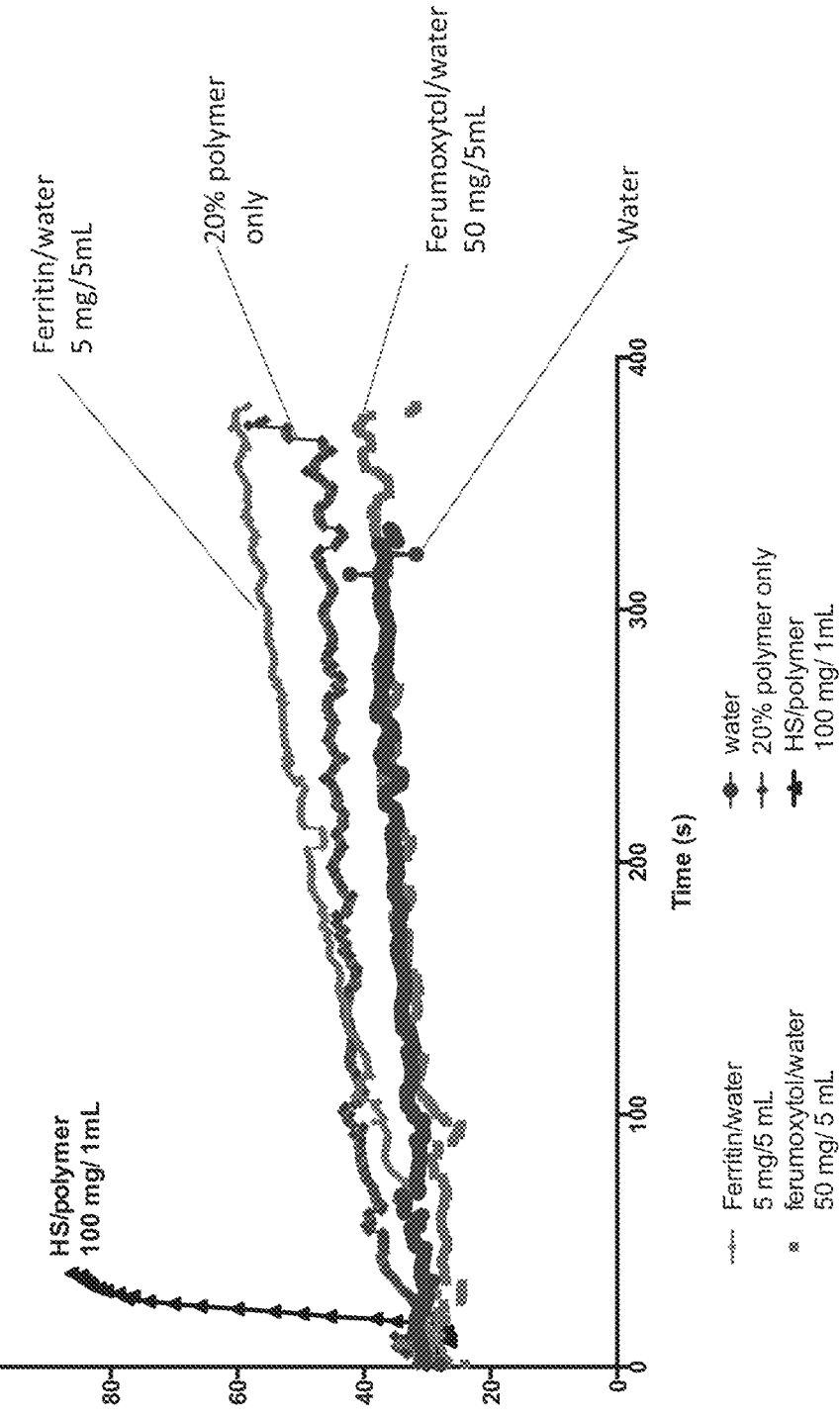
FIG. 2A shows effective rates of temperature increase by microwave heating for different fluids.

In its broadest form the invention includes application of a strong energy absorber, a 'heat substrate' (HS) or 'thermal accelerant' (TA) to a tissue site to locally modulate the rate, extent or endpoint of temperature increase to achieve effective hyperthermal ablation of the tissue with a microwave or radio frequency (RF) antenna, such as an image-guided transdermal microwave antenna, and overcome the limitations or problems raise by the limited range, high variance in temperature distribution and tissue-caused artifacts such as shadowing and heat sink. In one initial embodiment, a reverse phase polymer is used as a carrier and is injected as a fluid to desired locations in or around a relevant tissue site. The polymer is liquid, and it gels, becomes gelatinous or even solidifies at body temperature or above, so it either is, or quickly becomes, immobilized and stays localized at the delivery site. The polymer may be one that changes state and expels liquid (e.g., water) at temperatures consistent with ablation procedures. In one embodiment, the polymer also contains a salt; use of cesium chloride has been found to greatly increase the microwave/heating interaction and also to render the accelerant visible under CT or MRI, thus allowing image-guided verification of localization prior to RF or microwave excitation. Other imaging modalities, such as ultrasound may be used for image guidance. The polymer with appropriate characteristics may be one such as a block-co-polymer PLGA-PEG-PLGA consisting of polyethylene glycol, which is covalently esterified by an FDA-approved poly lactic-co-glycolic acid on both ends. In operation, a range of parameters may be varied to establish ablation response as a function of microwave conditions (i.e., power, frequency, ablation period and distance) in a representative tissue, such as a pig or calf liver. (see, for example, the modeling protocols in Pillai K, Akhter J, Chua T C, Shehata M, Alzahrani N, Al-Alem I, Morris D L. 2015. *Heat sink effect on tumor ablation characteristics as observed in monopolar radiofrequency, bipolar radiofrequency, and microwave, using ex vivo calf liver model.* Medicine (Baltimore) 94(9):e580). In another embodiment the thermal accelerant is a preparation of a serum albumin or other albumin, as described further below, together with certain electrolytes that condition its viscosity, microwave energy absorbance or thermal accelerant properties, and preferably also provide imaging under one or more medical imaging modalities such as MRI, ultrasound or x-ray CT imaging.

EXAMPLE 1

To mitigate the problem of inadequate heating, applicants devised a novel heat substrate to selectively increase heating and, by suitable placement, avoid undesirable cooling or 'heat sink' effects. This substrate is made of cesium chloride (CsCl) and is compounded in a reverse phase transition polymer to be positioned, and then activated by microwave energy from a distance. The reverse phase transition polymer, which may, for example be a PLGA-PEG-PLGA block copolymer of suitable viscosity, transforms into a gel at body temperature or above and with the cesium chloride salt strongly responds to microwave radiation and locally increases the temperature to more effectively ablate tumor cells that lie just outside of ablation zone AZ of FIGS. 1A, 1B and 1C. Furthermore, this heat substrate is an excellent contrast agent by itself, and was found to be visible under CT imaging. These properties make it particularly efficacious for treating solid tumors, where a physician can control the amount, the location(s) and the concentration of the heat substrate delivered to and fixed at locations about the targeted tumor to ensure complete ablation. Moreover, for larger or irregularly-shaped tumors, several microwave antennae may be positioned under image guidance to completely cover the tumor with a corrected/enhanced heat distribution.

Figure 2B:
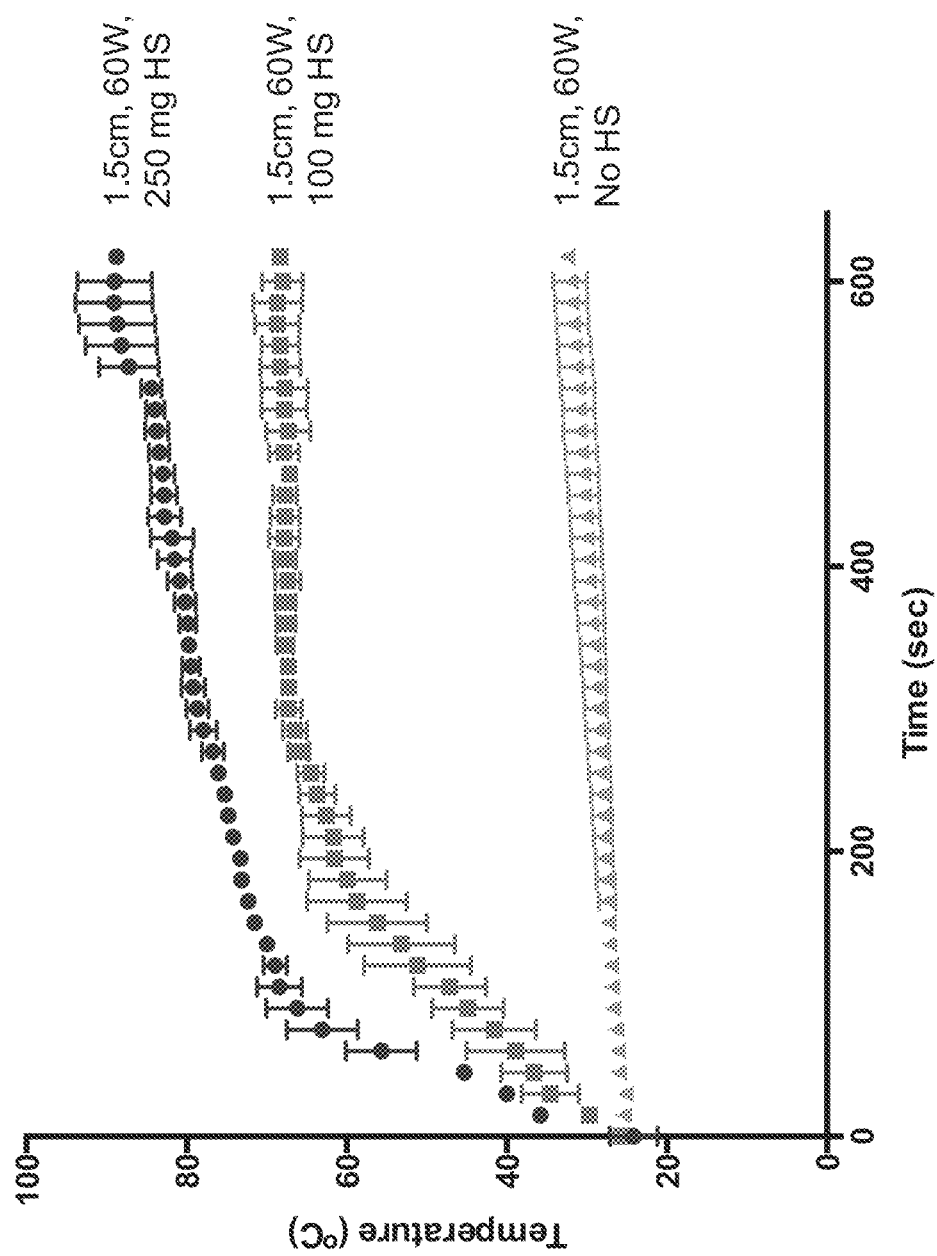
FIG. 2B shows effective rates of temperature rise for untreated tissue and for different heat substrate formulations.
Figure 2C:
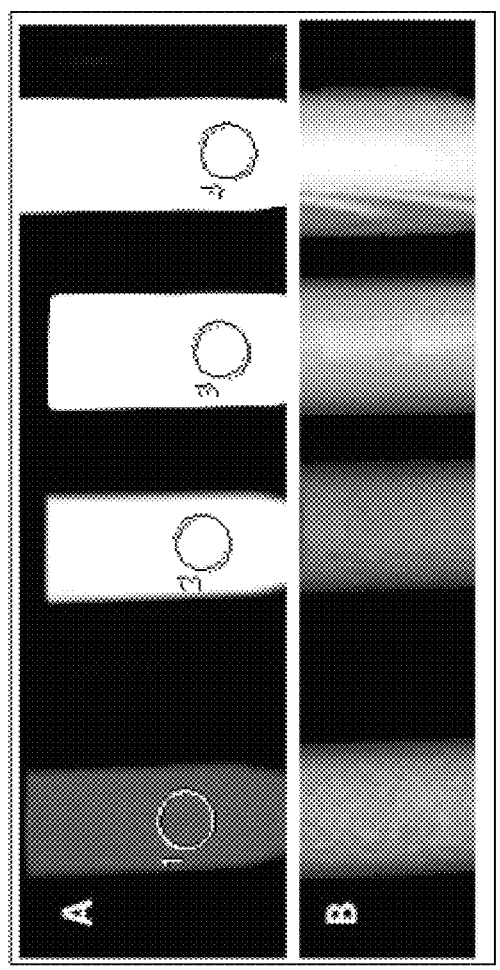
FIG. 2C shows small vials of distilled water and three different concentrations of a HS, confirming discernable contrast and detectability under CT imaging.

Various investigations were performed to assess the degree of heating achievable by the CsCl heat substrate compounded with different salt concentrations. FIG. 2A specifically shows that the heat substrate picks up microwave energy in a distance to augment heating, with high CsCl concentration of 100 mg/ml greatly increases heating measured near to (1 mm) the antenna, and that enhance heating with high uniformity is attained with other concentrations measured 15 mm away from the antenna (FIG. 2B). The Figures specifically illustrate the effect of heat substrate (100 mg/mL, CsCl/20% (w/v) polymer) on temperature increase by microwave energy (15 W, 915 MHz, t=400 sec) in FIG. 2A, where the temperature increase was monitored 1 mm away from the antenna; and the effect of heat substrate (0, 100, 250 mg/mL, CsCl/20% (w/v) polymer) on temperature increase by microwave energy (60 W, 915 MHz, t=600 sec) where heat substrate is deposited 15 mm from the MW antenna. There is a significant augmentation of heat when the heat substrate is present. Moreover the salt/polymer heat substrate is an excellent contrast agent visible through CT as shown in FIG. 2C. In that Figure fixed volumes of different concentrations of the salt preparation and of distilled water were imaged under CT and their Hounsfield absorbance noted to be: 1. Distilled water −15 Hu, 2. HS (10 mg/mL) 286 Hu, 3. HS (100 mg/mL) 2056 Hu, 4. HS (1000 mg/mL) 3070 Hu. The lower portion of FIG. 2C shows the same samples with computer-aided enhancement. Even the lowest concentration 10 mg/mL HS yields a discernable contrast comparing to water in CT. The imaging was performed using a GE Optima 580 W CT scanner with CT protocol: 120 kV, 50 mA, 0.8 second rotation, 0.562:1 pitch, and 16×0.625 mm detector configuration. The radiation output (CTDIvol) was 12.08 mGy, and the Dose Length Product was 193.88 mGy-cm.

Figure 2D:
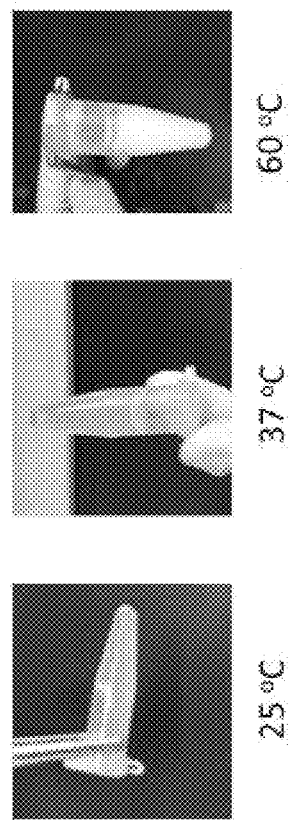
FIG. 2D shows a polymer/salt agent undergo liquid-gel-precipitate changes with temperature rise.

FIG. 2D illustrates the phase change properties with increasing temperature when the CsCl salt is compounded with polymer.

Temperature-time plots were made for different concentrations, together with pictures of the substrate changes when deposited and microwaved in an ex-vivo liver and these confirmed that the heat substrate is capable of heating liver tissue 15 mm away from the antenna, and that the substrate can be deposited as a liquid at ambient temperature and turns into a gel once in body, allowing the tumor boundary to be precisely targeted to ensure complete ablation. In that study a whole calf liver was heated with MW energy (60 W, 915 MHz): and a small 350 μL volume of 100 mg HS in 20% (w/v) polymer solution was injected to a point 1.5 cm away from the tip of the MW antenna. After 10 minutes, the area was cut open to observe the polymer solution transformed into a precipitate. The temperature increase was seen to be proportional to the HS concentration. At 250 mg/mL, the temperature reached 60° C. within 3 minutes. At 100 mg/mL, it took approximately 5 minutes whereas the temperature increase was nominal when no HS had been applied.

The investigations of Example 1 thus demonstrated the value of the heat substrate. Further investigations were designed and/or carried out to model or assess heating characteristics of the compositions in specific tumor tissues or specific distances, as well as evaluating imageability of representative formulations (see the discussion of FIG. 2C, supra) to better support use of the heat substrate in clinical procedures and new methods of treatment. Specifically, the heat substrate may be suitably positioned in relation to the microwave antenna, so that application of microwave energy produces a tailored heating profile to heat up and ablate the surrounding tissue. For example, the accelerant may be positioned somewhat away from the antenna to enhance heating of peripheral tissue which is too distant to be fully or uniformly ablated using a single microwave antenna alone. The thermal accelerant can also be positioned to prevent the heat loss (also known as "heat sink" see FIG. 1C—that would otherwise occur due to the presence of a large blood vessel in or adjacent to the intended ablation zone, trapping an effective level of heating in the near field without ablating the blood vessel itself. Modeling was performed for the use of multiple antennae, and for more than one localized body of thermal accelerant strategically placed to define a larger, or more uniform and expanded ablation zone, or to define an ablation zone while limiting the time that power is applied to other portions of the organ. Thus the thermal accelerant plays a cooperative and synergistic role in augmenting the effective microwave energy. The suitability for each of these interventions, however, will require that the actual level of increased heating be sufficient to overcome any countervailing conduction and absorption effects exerted by surrounding tissue.

A pilot study was designed to establish the actual thermal accelerant response as a function of microwave conditions (i.e., power, frequency, ablation period and distance) in pig's liver. Ideally, the thermal accelerant augments the microwave energy transmitted through the antenna, and it was expected that the thermal accelerant turns into a gel, once injected, in the target area of the body. Upon application of the microwave energy, the thermal accelerant will heat up the surrounding tissue, which is too distant to be ablated with single microwave antenna alone.

Figure 3A:
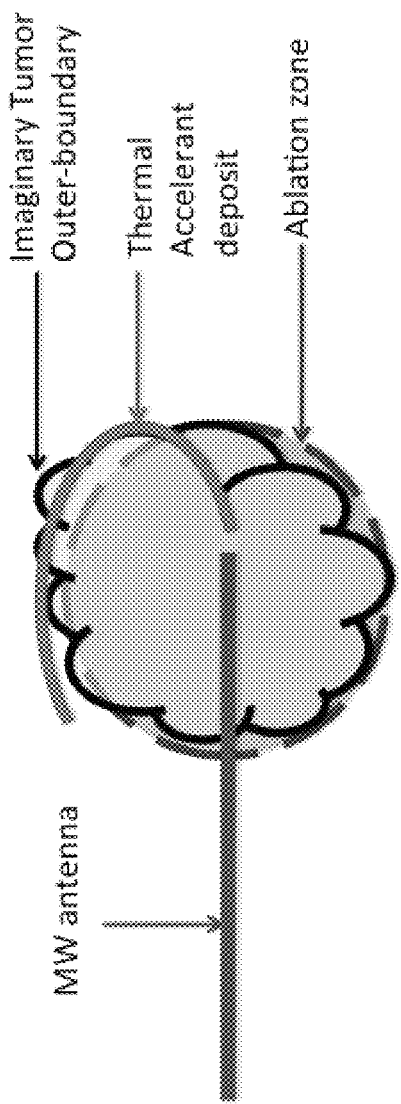
FIG. 3A schematically shows a tumor and placement of antenna and thermal accelerant.
Figure 3B:
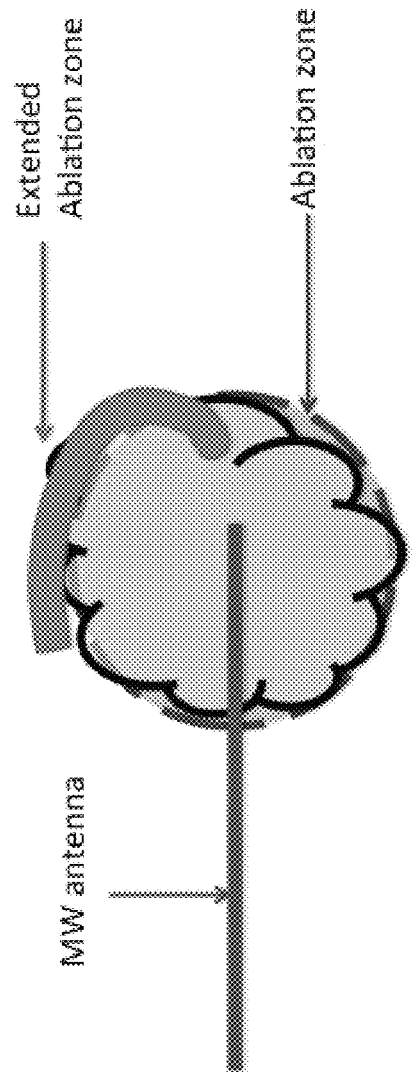
FIG. 3B shows extension of ablation with the placement of FIG. 3A.
Figure 4:
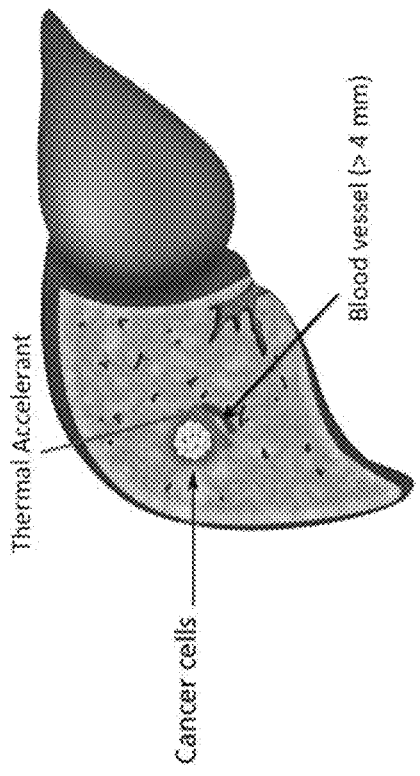
FIG. 4 shows a liver section and placement of thermal accelerant between a tumor and a blood vessel.
Figure 5:
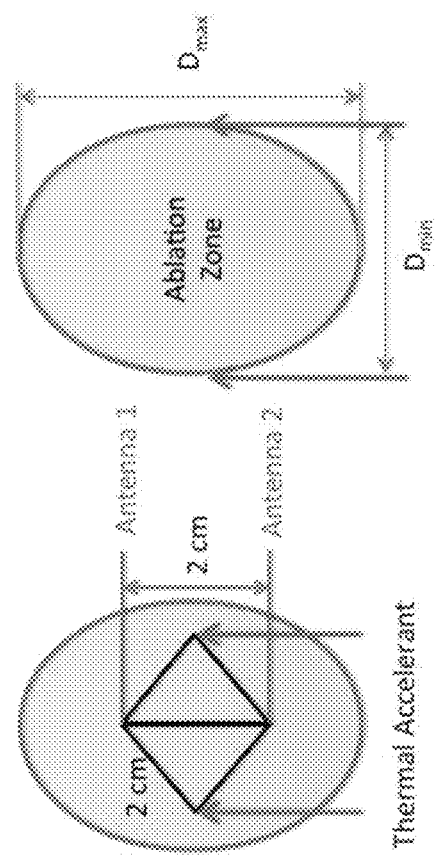
FIG. 5 shows placement of two antennas and two sites of thermal accelerant for creating an enlarged ablation zone.

This situation is illustrated schematically in FIG. 3A and FIG. 3B wherein a small mass of the substrate located at the upper right distal region or surface of an irregular tumor (FIG. 3A) and outside of a theoretical circular or symmetric effective ablation zone centered on the microwave antenna, produces a well-defined ablation region (thick band, as seen in FIG. 3B), extending the region of complete ablation to or beyond the tumor boundary. The study was further designed to test the notion that the thermal accelerant can help avoid the heat loss (also known as "heat sink") caused by a blood vessel adjacent to the ablation zone, without ablating the blood vessel itself. This situation is illustrated in FIG. 4, which identifies where to place the thermal accelerant to enhance tumor ablation while avoiding damage to the vessel. FIG. 5 illustrates placement of thermal accelerant and multiple microwave antennas to create a wider and taller ablation region of uniform intensity, showing that if multiple antennae and thermal accelerant are strategically placed, the ablation zone can be expanded. This is to demonstrate a cooperative and synergistic role that the TA plays in augmenting the heating by microwave energy.

FIGS. 3A and 3B schematically diagram the microwave ablation, wherein a thermal accelerant is injected to an imaginary tumor target area. A typical ablation zone is about 2.5 cm in diameter when a single antenna is used with the microwave ablation conditions: 915 MHz, 60 W for 10 minutes. The thermal accelerant stays as deposited since it turns to a gel at body temperature. The track of the thermal accelerant gel is shown just outside of the nominal ablation zone, and runs through the outer-boundary of the imaginary tumor in the liver. FIG. 3B shows the coagulative ablation zone extended by augmentation of the microwave energy.

FIG. 4 shows an experimental set-up wherein the thermal accelerant deposited between a major blood vessel (>4 mm in diameter) and the ablation zone to see if the heat loss will be minimized. Because the microwave energy is augmented between the antenna and the thermal accelerant, shorter antenna actuation can achieve complete ablation of the tumor, and the blood vessel itself will be protected from being ablated.

FIG. 5 shows multiple antennae and bodies of thermal accelerant strategically placed to maximize an ablation zone. When two antennae are placed 2 cm apart (d=2 cm) and the two thermal accelerants are placed 2 cm from each antenna to form a rhombus (in cross-sectional view), application of the microwave energy (illustratively total 120 W, 60 W each antenna) for 10 minutes will result in the larger ablation zone than control (d=2 cm, MW only) and a known case of d=1.5 cm (i.e., 915 MHz, 60 W each, 10 minutes, Dmax=3.5 cm, and Dmin=3.3 cm). This demonstrates a cooperative and synergistic role of TA in augmentation of the microwave energy.

A brief discussion of the Thermal Accelerant and the underlying technical considerations may be useful for understanding the scope of materials and effects of the invention and improvements in microwave ablation technology.

The novel MWA methodology is intended to achieve the complete ablation of tumors. The methodology utilizes a thermal accelerant which in one embodiment is comprised of cesium chloride (CsCl) and a reverse phase transition polymer with the following rationale: Tissue ablation by MW energy primarily operates by kinetically exciting water molecules to generate heat. A water molecule is structurally bent (104.5°) due to two non-bonding electrons on oxygen atom, and thus has a relatively high dipole moment (1.85 D, D=Debye). At the MW frequency region (300 MHz-30 GHz), water molecules synchronize to the alternating electrical field to cause collisions among themselves, and this energy is converted into heat. Most of alkali and alkaline earth metal ions tend to have high dipole moments (D>7-8, e.g., KBr 10.4 D, BaO 7.9 D), suggesting that these compounds can generate heat more effectively than water molecules. Among these ionic compounds, cesium chloride (CsCl) is particularly interesting not only because of its high dipole moment (10.4 D), but because of its unique physicochemical and toxicological properties that it offers for MW ablation: First, CsCl is highly soluble in water (1,865 kg/L at 20° C. and 2.7 kg/L at 100° C.). This means that a highly concentrated CsCl thermal accelerant solution can be made if necessary; second, with its high atomic number and density (Z=55 and d=3.99 g/mL), the Cs ion can provide an excellent contrast in CT. This is particularly useful for our purpose since CsCl can be used as a substrate for image-guidance; thirdly, CsCl is non-toxic (LD50=2,600 mg/kg, oral, 910 mg/kg iv, rat). The polymer component possesses the unique property of being a liquid at ambient temperature, but a gel at typical body temperature (35-37° C.). Moreover, upon a further increase in temperature, the polymer precipitates by expelling water molecules from the polymeric lattice structure. The polymer is considered safe, and consists of polyethylene glycol (PEG) that is esterified by a FDA approved poly-(lactic-co-glycolic) acid (PLGA) on both ends. The polymer is biodegradable and biocompatible. CsCl is an ionic compound and, thus, miscible with the aqueous polymer solution to give homogeneous distribution of CsCl permitting uniform heating within the target ablation space.

Using CT for image guidance, the desired amount of the thermal accelerant with known CsCl concentration can be deposited in the boundary of the tumor mass. Subsequently, the injected heat substrate turns into a gel of predetermined ablation shape and volume. The heat substrate gel will be heated by MW energy transmitted through an MW antenna (MicrothermX® Perseon Medical, Salt Lake City, Utah) to reach tumoricidal temperature (>60° C.) in the targeted area.

EXAMPLE 2

Preliminary Study: Augmentation of Microwave Energy

Figures 6A, 6B:
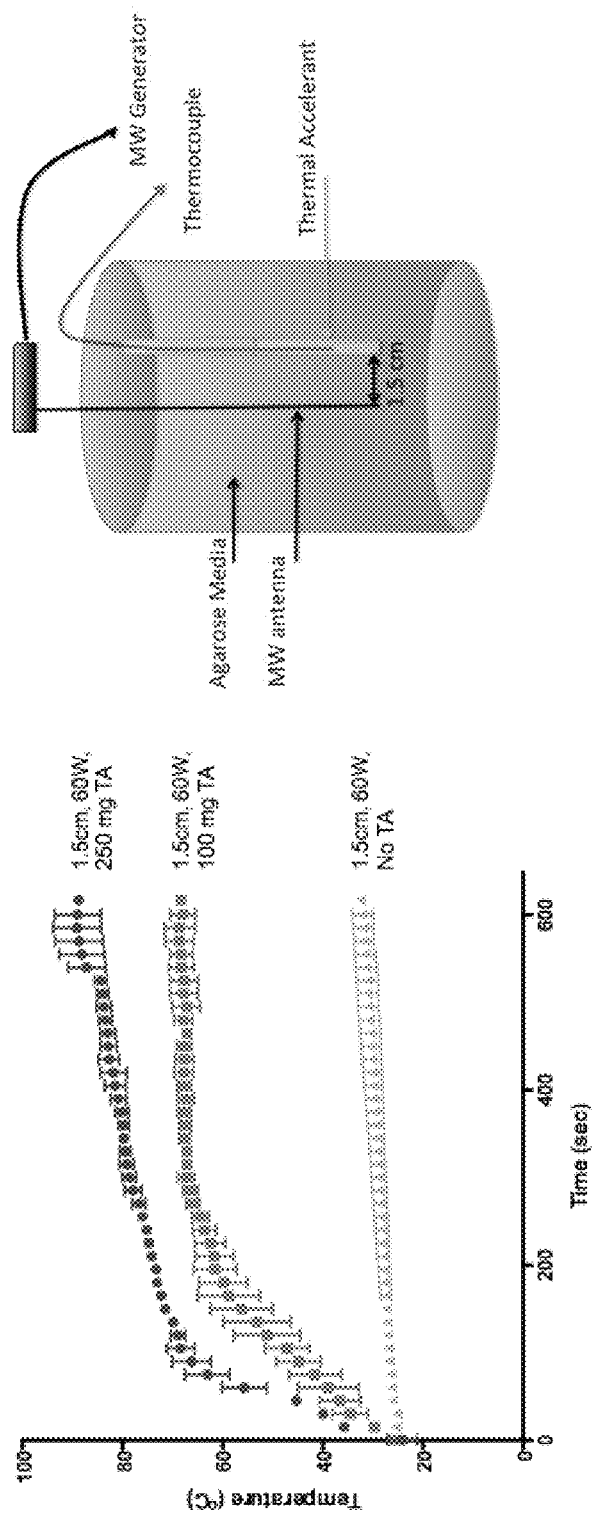
FIG. 6A shows an experimental setup used to evaluate heat augmentation of a thermal accelerant.
FIG. 6B is a Time/Temperature chart of heating for different amounts of the accelerant.

As a proof of concept, we tested the efficiency of the heat substrate in augmenting the microwave energy. Using a phantom (1% (w/v) agarose medium), temperature increase by a control and the heat substrate (two concentrations: 100 mg/mL and 250 mg/mL, respectively) was measured over time. Under the MW conditions (60 W, 915 MHz, 10 minutes), a maximum ablation zone attained is typically 2.5 cm in diameter (i.e., a zone extending a distance 1.25 cm from the antenna). This distance and the conditions were used as a baseline platform to evaluate the augmentation efficiency of the heat substrate. As depicted in FIG. 6B the heat substrate was placed at 1.5 cm from the antenna, and was heated by MW energy transferred through an MW antenna (MicrothermX® Perseon Medical, Salt Lake City, Utah) to reach tumoricidal temperature (>60° C.). Temperature plots are shown in FIG. 6A. The thermal accelerant was found to augment the MW energy in a concentration dependent manner and reached beyond 60° C. within 5 minutes (c. 1 minute 250 mg/mL; <3 minutes 100 mg/mL, respectively) in comparison to the sample without the thermal accelerant. FIG. 6A shows a typical set up for the in vitro experiment.

EXAMPLE 3

A preliminary study of the thermal accelerant as a CT contrast agent was carried out. Various concentrations of the thermal accelerant (TA) solutions were prepared and measured for their CT contrast. FIG. 2C shows the TA solution with the concentration as low as 10 mg/mL produced a discernable contrast as compared to water. The degree of the CT contrast was found to be proportional to the concentration of the thermal accelerant (TA), so the TA solution is CT visible. The upper portion of FIG. 2C shows four samples 1)-4) as follows: 1. Distilled water −15 Hu, 2. TA (10 mg/mL) 286 Hu, 3. TA (100 mg/mL) 2056 Hu, 4. TA (1000 mg/mL) 3070 Hu. The lower portion of FIG. 2C shows the same samples with computer-aided enhancement. The lowest concentration 10 mg/mL TA yields a discernible contrast compared to water in CT. GE Optima 580 W CT scanner. Used CT protocol: 120 kV, 50 mA, 0.8 second rotation, 0.562:1 pitch, and 16×.625 mm detector configuration. Radiation output (CTDIvol) was 12.08 mGy. Dose Length Product was 193.88 mGy-cm.

EXAMPLE 4

Reverse Phase Transition Polymer.

The polymer used with the thermal accelerant desirably has the property of being a liquid at ambient temperature, but a gel at typical body temperature (35-37° C.). Upon a further increase in temperature, the polymer precipitates by expelling water molecules from the polymeric lattice structure as shown in FIG. 2D supra. The polymer of this example is technically a block-co-polymer that is made of poly(lactic-co-glycolic acid) (PLGA) and polyethyleneglycol (PEG). PLGA is a FDA approved polymer for its biocompatibility like PEG. The polymer used as a heat substrate component here is structurally arranged as follows: PLGA-PEG-PLGA. At ambient temperature (25° C.), the polymer is conformed in such a way that a PLGA interacts with the intramolecular PLGA to form a hairpin. This conformation will change as the temperature increases so that intermolecular PLGA-PLGA interactions predominate (37° C.). Upon further heating (>60° C.), the conformation will be changed back to the hairpin conformation except that water molecules are expelled out of the polymer layer at higher temperature.

EXAMPLE 5

Ex Vivo Experiment Augmentation of MW Heating by the Heat Substrate in a Whole Calf Liver.

A whole calf liver was heated with MW energy 60 W, 915 MHz: A small volume (350 μL) of 100 mg CsCl in 20% (w/v) polymer solution was injected to a point 1.5 cm away from the tip of the MW antenna. After 10 minutes, the area was cut open to observe the polymer solution transformed into a precipitate. The temperature was plotted showing the temperature increase to be proportional to the TA concentration. At 250 mg/mL, the temperature reached 60° C. within 3 minutes. At 100 mg/mL, it took approximately 5 minutes, while without TA the temperature increase was nominal.

Figure 7:
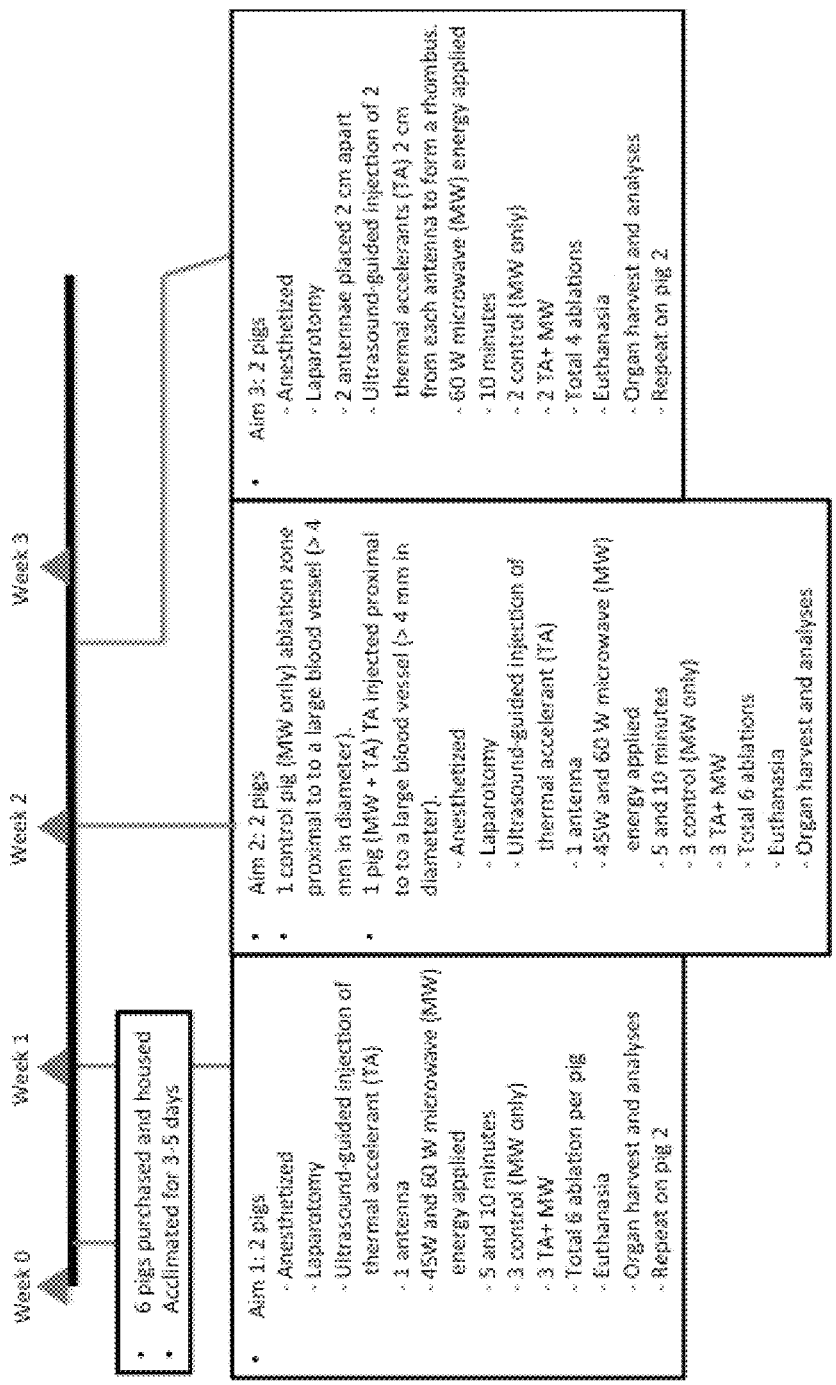
FIG. 7 is a chart of an investigational in vivo animal protocol designed to identify effective ablation materials, parameters and operating procedures.

The foregoing observations and measurements provided substantial confirmation of the underlying concepts, and further motivation to pursue in vivo animal investigations which could identify the magnitudes of any effects due to live-subject tissue conditions, such as perfusion effects or corrections for blood flow in a vessel, and establish variances in ablative results. In such a study ('a pilot study') would have as Specific Aims one or more of the following: Aim 1) Laparotomy will be performed on a pig, and the liver will be exposed. Using ultrasound as image-guidance, the microwave (MW) antenna will be inserted and the microwave energy of the preset parameters will be applied. Similarly, the thermal accelerator (TA, 250 CsCl mg/mL of 20% (w/v) polymer solution) is injected to the liver parenchyma, an imaginary target area using ultrasound as image-guidance and deposited as a stationary gel. The MW antenna will be inserted approximately 1.5 cm away from the thermal accelerant. The microwave energy of the same parameters will be applied to the antenna (i.e., 915 MHz, 45 or 60 W for 5 to 10 minutes). All animals will be euthanized immediately after the procedure, and the liver will be harvested for further comparisons including CT and analysis of the ablation patterns and measurement of the ablation volume; Aim 2) As described in Aim 1), the animals are anesthetized and laparotomized to expose the liver. With ultrasound guidance, the antenna will be placed 1.5 cm from a large blood vessel and ablated with the preset conditions (915 MHz, 45 or 60 W for 5 to 10 minutes) on the first pig (control). In the second pig's liver, the antenna will be placed 1.5 cm from a large blood vessel after the thermal accelerator is injected near the blood vessel, and then the microwave energy is applied. Each pig will receive three ablations: 1) 45 W for 10 minutes, 2) 60 W for 5 minutes, 3) 60 W for 10 minutes. Immediately after the procedure is complete, the pigs are euthanized to harvest the liver for CT and analysis of the ablation patterns and measurement of the ablation volume by depth, height, and width; Aim 3) A pig liver will be exposed after laparotomy is performed on a pig under anesthesia. Using ultrasound as image-guidance, two antennae will be inserted in the liver 2 cm apart and the microwave energy (60 W) will be applied for 10 minutes for control. In the same liver, two antennae will be inserted 2 cm apart, and followed by two injections of the thermal accelerant (TA) by which the injection is made 2 cm away from each antenna to form a rhombic shape as depicted in FIG. 3. The microwave ablation will be performed under the same conditions as control (i.e., 60 W, 10 minutes). After the procedure is complete, the pigs are euthanized to harvest the liver for CT and analysis of the ablation patterns and measurement of the ablation volume by depth, height and width. FIG. 7 is a chart showing a proposed investigative protocol.

Briefly, the Aim 1 is intended to examine heat augmentation efficiency of the thermal accelerant (TA) in percutaneous microwave ablation using a single antenna, while Aim 2 is intended to assess efficacy for overcoming heat sink effects, and Aim 3 investigate the TA being used for situations that may have been addressed previously by using an extra antenna.

As described above, the thermal accelerant was conceived In order to mitigate the incomplete ablation issue, and envisions a novel thermal accelerant (TA) that can augment the microwave energy from a distance unreachable by a single antenna alone. This helps not only extending the ablation zone covering the outer-boundary of a tumor mass but also ablating more rapidly. As clinically shown, more effective and faster microwave ablation helps the procedure be more complete, thus lowering rate of tumor recurrence rate. In addition, TA can be injected strategically near a heat sink so that the heat loss can be prevented.

The TA, for best utility in image-guided thermal ablation to treat tumor, preferably has the following properties: 1) it can augment the electromagnetic radiation energy (e.g., radiofrequency, microwave), especially from a distance unattainable by a single antenna; 2) it is visible under various imaging modalities (e.g., computed tomography (CT), ultrasound or MRI); 3) it is injectable, and is stationary once injected; and 4) it is non-toxic.

As described above, a synthetic polymer with an alkali rare earth salt (CsCl) has been found useful, however other polymer materials, such as albumin, offer similar benefits, and the viscosity properties and other traits of a human blood serum albumin or similar preparation can be further tailored by concentration, salt content and other steps. Generally, the components of the TA may include three, non-toxic components: 1) a polymer (natural or artificial) as a carrier; 2) an ionic component for overall charge and viscosity balance; 3) an imaging component. With the optimal compositions of the three components, TA can be deposited at the target area of the tumor under image-guidance (e.g., US, CT or MRI), and be able to augment the applied energy (e.g., microwave, radiofrequency or electroporation) to better achieve complete ablation. For example, TA comprised of bovine serum albumin (BSA), NaCl and tantalum powder satisfy the aforementioned criteria, to provide more effective ablation resulting in elimination of untreated outer-boundary of tumors and the heat sink effect. The salt adjusts the charge distribution within the albumin, while tantalum enhances its imaging characteristics. For magnetic resonance imaging the preparation demonstrates signal decay rate time constants ($T_1$) shorter than many tissues. As an example, liver at 3 Tesla has $T_1$ of approximately 800 ms. The albumin/NaCl preparation has $T_1$ in the range of 250 ms to 330 ms, depending on the concentration of NaCl. In a $T_1$-weighted MRI scan for image guidance, the TA will show substantially brighter than surrounding tissue (positive contrast) allowing for unambiguous positioning of the material. $T_2$ contrast mechanisms can also be used, primarily via negative contrast in which the TA has shorter $T_2$ than surrounding tissue and $T_2$-weighted scans are used for guidance.

Albumins belong to a globular protein family, which are water-soluble, moderately soluble in concentrated salt solutions, and experience heat denaturation. Albumins are commonly found in blood plasma and differ from other blood proteins in that they are not glycosylated. A number of blood transport proteins are evolutionarily related, including serum albumin, alpha-fetoprotein, vitamin D-binding protein and afamin. Serum albumin is the most abundant of human blood plasma. It binds water, cations (E.g., $Ca^{2+}$, $Na^+$ and $K^+$), fatty acids, hormones, bilirubin, thyroxine and pharmaceuticals (including barbiturates and taxol). Its main function is to regulate the colloidal osmotic pressure of blood. The isoelectric point of albumin is 4.9 (of human serum albumin, Ip=4.7).

Albumin is comprised of 3 domains of similar structure, which all originated from the same domain. Each domain is composed of ten α-helices and can be further divided into two subdomains, denoted as A and B, containing 6 and 4 helices, respectively. The two subdomains are connected by a long amino acid loop, which is responsible for the change in orientation of the subdomains. On the other hand, the conformational flexibility between domains depends on the bending of the helices. Its canonical structure is supported by a conserved set of 17 disulfide bridges, which are maintained in all mammalian serum albumins. Of the 3 domains, the first domain is the only one to contain 5, not 6, disulfide bridges, missing one at Cys-34. Instead, the lack of an intramolecular disulfide bridge forming at Cys-34 allows albumin to dimerize with another albumin molecule at this residue. HSA, BSA, LSA, and ESA have exchanged 70-85% of their residues over the course of 500 million years, however the positions of the cysteines and disulfide bridges have not changed. Additionally, although the domains have undergone significant evolutionary changes, their overall architecture and secondary structure elements have remained unchanged.

FIG. 8A and FIG. 8B illustrate the surface potential of HSA (A) and BSA (B), with different colors representing positively and negatively charged areas. Vincent Goovaerts et al., *Phys. Chem. Chem. Phys.*, 2013, 15, 18378-18387. Mature BSA contains 583 amino acids and has 99 positive (K, H, R) and negative (D, E) residues. Similarly, mature HSA contains 585 amino acids and has 99 positive (K, H, R) and 98 negative (D, E) residues. Although the general structure of the protein is conserved among mammalian serum albumins, there are significant differences. In sequence, BSA shares only 75.8% homology with HSA. Their structures are canonical (due to the conserved disulfide bridges), but differ in surface amino acids. As a result, the ligand binding pockets in the various serum albumins show different amino acid compositions and slightly different conformations, allowing for the binding of different ligands.

The tantalum component of TA is a high radiopaque material that provides fluoroscopic visualization. Tantalum is an inert metal with a history of use in implants requiring incorporation of a contrast agent, such as arterial stents, hip prostheses, and embolization materials. [9, 10] In addition to its use in embolization materials, tantalum powder has been used as a contrast agent injected into the cervical spinal cord for visualization during percutaneous cordotomy. Additionally, tantalum powder has found uses in neurosurgery, to mark the plane of section in lobotomy or leucotomy, to provide visualization or definition of a site for tumor removal, and for detection of recurrent subdural hematoma after surgery.

Although the properties of serum albumin have been extensively studied under physiological conditions studies on the highly concentrated albumins (i.e., 300 mg/mL), especially, as a carrier of an imaging contrast agent or a thermal accelerant are rare. Nonetheless, calculated dipole moment of serum albumin in vacuum is very large, 710 D (D=Debye) in comparison to the TA substance first-described above, CsCl (ca. 10 D) or compared to water (1.85 D). Despite its large dipole moment, physiologically available bovine serum albumin (BSA) alone does not increase the temperature rapidly due to its low dielectric constant and the loss factor in the range of frequencies of interest, i.e., 915 MHz-2.45 GHz. [12] With 500 mg/mL BSA, a gradual increase to 40-50° C. was observed in vitro at 10 min for 60 W with a 915 MHz when the antenna was positioned a distance of 1.5 cm from the BSA sample. The temperature increase was insufficient to make BSA alone as a TA. Furthermore, the albumins of high concentrations (>300 mg/mL) tend to have a very high viscosity due, in most part, to protein-protein interactions as shown in FIG. 9 which schematically illustrates the viscosity of BSA as a function of concentration.

Figure 10B:
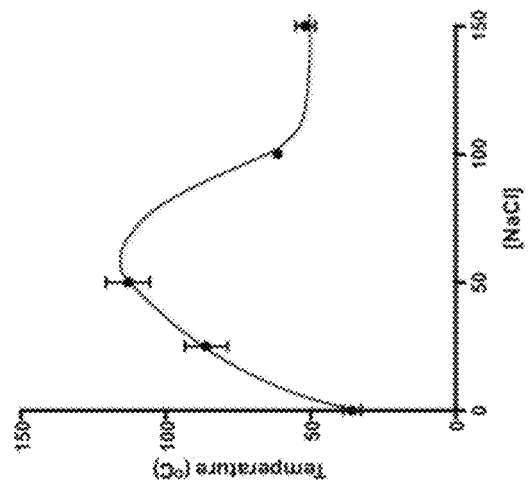
FIG. 10B shows the end-temperature increase at 120 seconds as a function of the NaCl concentration.
Figure 10A:
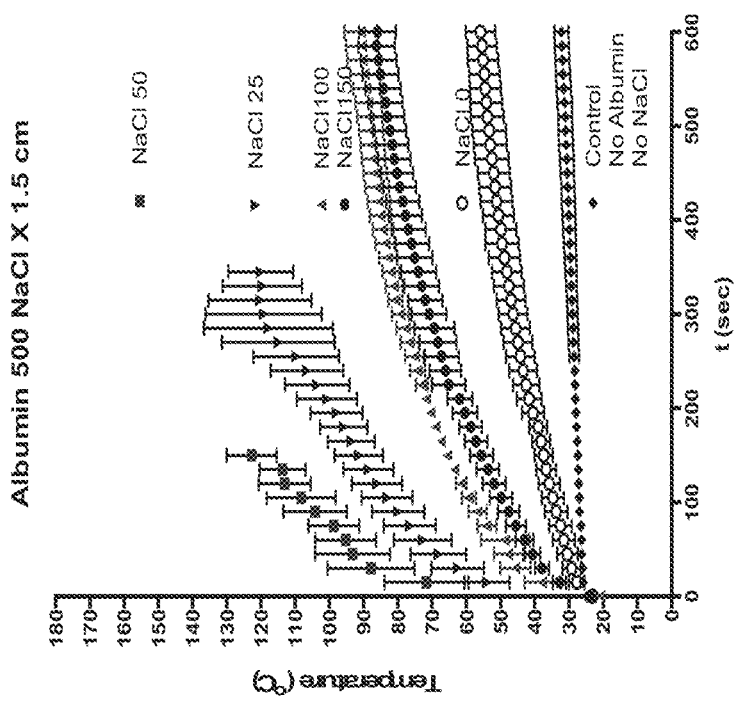
FIG. 10A shows temperature increase over time of a control and of albumin TA having different amounts of NaCl positioned 1.5 cm from a microwave antenna.

Under the applied microwave radiation, the surface charges of the albumin molecule are occupied by the intermolecular interactions with the readily available other albumin molecules. In order to relieve the interactions, we used NaCl as a chaotrope. In essence, it is believed that the intermolecular interactions of BSA molecules consist of charge-charge, dipole-dipole as well as hydrophobic interactions, and thus exhibit high viscosity. By adding NaCl to the solution, the viscosity will be lowered by the salt ions competing with other BSA charges and subsequent solvation by water molecules. This will free up the individual BSA molecules to respond to the microwave energy. We have examined the effect of [NaCl] on thermal acceleration efficiency of the albumin (500 mg/mL), and the results are shown in FIG. 10A. The concentration of NaCl inducing the optimal TA efficiency is slightly higher than 50 mg/mL but less than 75 mg/mL. The higher concentrations suppress the efficiency (>75 mg/mL NaCl), and has a solubility limit beyond 230 mg/mL. At the optimum NaCl range, the viscosity of the albumin solution (500 mg/mL) also was reduced to about 30 cP (centiPoise) from about 70 cP (estimated), which provides the flow comparable with that of ethiodized oil such as poppyseed oil. FIG. 10A shows the effect of various NaCl concentrations on microwave ablation (MWA, 60 W, 915 MHz, 10 minutes, distance from the antenna=1.5 cm). FIG. 10B is a schematic plot of temperature v. [NaCl] concentration at the 120 second endpoint under the same microwave regimen, showing a temperature peak at around 50 mg/mL NaCl.

Albumin thermal accelerant as described above was used in a number of in vivo microwave ablation experiments in pigs and the ablated sites were stained with triphenyl tetrazolium chloride to distinguish dead from viable cells. The images from these further experiments demonstrated that MWA with TA yields a larger ablation zone than control using a typical microwave ablation (915 MHz, 60 W, 10 minutes d=1.5 cm) without TA as a control. Under the same MWA conditions, TA (1 mL of albumin (500 mg), NaCl (50 mg)) generated a larger ablation zone unaffected by a large blood vessel (1 cm in diameter). A MWA was performed on the left medial lobe of the swine liver (915 MHz, 60 W, 10 minutes d=1.5 cm). Under the same MWA conditions with TA (1 mL of albumin (500 mg), NaCl (50 mg)) generated a larger ablation zone on the same lobe of the liver. A MWA on the left medial lobe of the swine liver (915 MHz, 60 W, 10 minutes, d=1.5 cm) was compared to a MWA with TA (1 mL of albumin (500 mg), NaCl (50 mg) injected behind the blood vessel. For that procedure the ablation zone was seen to extend through the blood vessel (>4 mm in diameter) completely surrounding the blood vessel. In tandem with the previous example, this demonstrated that MWA with TA is able not only able to augment the microwave energy but also to block the heat loss caused by the "heat sink" effect. In an additional experiment, an ultrasound image was taken immediately after ablation was complete (10 minutes), with the blood vessel positioned in between the antenna and TA. During the ablation, blood flow in the vessel was seen to be normal, which indicates that the microwave energy was able to penetrate through the functioning blood vessel and operate effectively in the far field without overheating the vessel. This suggests that the "heat sink" effect can be eliminated by the ablation methodology. Other TTC-treated kidney tissue images show a typical ablation zone using a single antenna with 60 W, 915 MHz, for 10 minutes, and the ablation is slightly off-centered as the connective tissues in the central renal sinus area are less affected. The resultant ablation zone is about 1 cm in diameter. TA was able to produce a drastic increase of the ablation zone (3 cm in diameter) where the central tissues were also shown to be completely ablated (60 W, 915 MHz, 10 minutes; the distance between antenna and TA was 1.3 cm).

Figure 11:
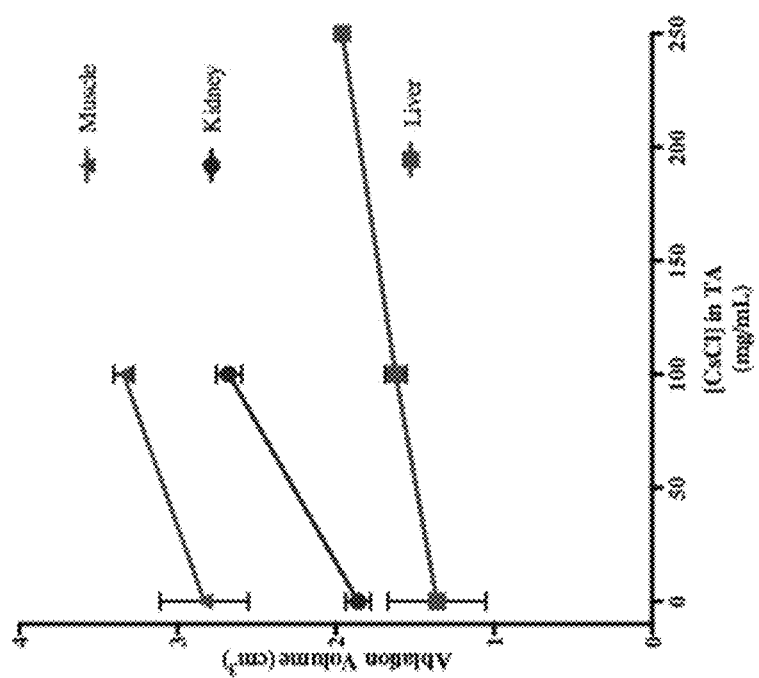
FIG. 11 shows increased ablation volumes achieved in different tissues using different concentrations of a Cesium Chloride component.

FIG. 11 show the results of further tissue ablation experiments done to assess ablation volumes in $cm^3$ for 1 mL of the thermal accelerant in different tissues (kidney, muscle and liver) with no TA or 1 mL of the TA at different concentrations of CsCl absorber. In each case the effective ablation zone was greater with the TA. Different concentrations of TA were tested with concentrations up to 250 mg/mL for the liver tissue ablation, as the liver is a key organ for treatment by this method. The other tissues also showed significant ablation volume increases.

As described above, the heat substrate or thermal accelerant of the present invention can be implemented in various forms or concoctions, and may involve tailoring the physical characteristics of a natural or artificial polymer to improve their utility as injectable, fixable, imageable and heatable media. Several strong initial materials have been described, but simple testing can quickly reveal or confirm additional ones. Thus, in addition to or in place of the cesium chloride microwave accelerant, other halides such as the bromide or iodide, and other alkaline or alkaline earth cations that are medically useful may be expected to offer similar if not comparable ablation enhancement. For example Rubidium chloride, or a suitably protected rubidium portion may be useful. Similarly, in addition to BSA and PLGA-PEG-PLGA polymers, materials in alginate media, or salts having anions such as carboxylate or sulfite materials may be employed if they exhibit suitable characteristics, and a discussion of useful cations, anions or electrolyte or other materials for optimizing the desired physical imaging, heating and other characteristics of the thermal accelerant are included above. By way of example, various embolization media can be so modified, and their basic emulsion-like composition will also provide ultrasound imageability. Further, formulation of albumin with sodium chloride salt has been shown to provide a low-viscosity thermal accelerant having appropriate physical characteristics for diverse tissue treatments (including intravascular) with good microwave heating performance, while being completely biocompatible. Different ones of the described thermal accelerants may be appropriate for different microwave regimens of 400 MHz, 915 MHz, 2450 MHz, or 5800 MHz range, and may be used if they are medically safe and result in effective microwave ablation enhancement characteristics for the tissue, tumor mass or organ under consideration.

In addition, the described polymer can be delivered to a vessel in the target tissue and heated to act as an embolization substance to block a vessel that feed the target tumor to thereby cause tumor regression by cutting off oxygen and nutrients supply through the vessel. A further variation is to add one or more anticancer drugs or treatment agents to the polymer, so that once localized and heated the polymer serves as an in-situ time-release treatment agent.

The invention described herein involves the ablation methodology of creating thermal lesions by augmentation of the electric or electromagnetic energy, e.g. absorption of radiated energy and conversion into thermal energy. The ablation methodology includes a thermal accelerant (TA) that functions as a satellite energy absorber, e.g., to increase the heating effect. The thermal accelerant (TA) is preferably comprised of three components, 1) polymer (natural or artificial) as a carrier; 2) an ionic component or equivalent for overall charge and viscosity balance; 3) an imaging component which allows the ablation procedure to be monitored.

Other polymers may include either natural or artificial, for example, albumins, silk, wool, chitosan, alginate, pectin, DNA, cellulose, polysialic acids, dendritic polylysine, poly (lactic-co-glycolic) acid (PLGA). The ionic component may include, $M^+X^-$ or $M^{2+}Y^{2-}$, where M belongs to alkaline or alkaline earth metal such as Li, Na, K, Rb, Cs and X represents halogens, acetate and other equivalent counter balance to $M^+$, and Y can be $X_2$ or mixed halogens, acetates, carbonate, sulfate, phosphate and other equivalent counter balance to $M^{2+}$. Other organic components can independently affect these roles. See: Wang, S. et al, Mol. Pharmaceutics 2015, 12, 4478-4487. For CT imaging, cesium, tantalum, iohexol, ethiodized polymers such as PLGA, PEG, albumin can be utilized, while for ultrasound imaging, polymers have been found to be in general hypoechoic. However when PLGA-PEG-PLGA (a block co-polymer, a reverse phase-transition hydrogel) is used, the polymer appears hypoechoic immediately after injection subsequently turns into hyperechoic as temperature increases. A similar observation was made when albumin is used as a carrier polymer.

Upon application of electromagnetic energy to drive ablation (e.g., microwave, RF, electroporation), remotely deposited TA can absorb the energy much more effectively than the surroundings and help extend the ablation zone. Remotely deposited TA, here means at a distance greater or equal to 1.5 cm from the antenna open slot, when the conditions (60 W 915 MHz for 10 minutes) are used as reported in Appendix C. As described above, upon application of the electromagnetic energy (e.g., microwave, RF, electroporation) TA deposited adjacent to a large blood vessel can prevent the ablation target from suffering excessive heat loss, therefore TA can mitigate the "heat sink" effect to provide complete ablation. In addition, TA can be used in embolization/ablation combination treatments to destroy tumors. TA has a viscosity similar viscosity to Lipiodol, thus can be delivered via an intravascular catheter to be deposited accurately. A subsequent ablation can destroy tumors effectively.

Thus, as an overview and recapitulation, the thermal accelerant (TA) formulations and materials described above can function as satellite energy absorbers to create thermal lesions by augmenting the coupling of the electric or electromagnetic energy into heat at distances not effectively treatable by an antenna alone. The TA may be comprised of three components, 1) polymer (natural or artificial) as a carrier; 2) an ionic component or equivalent for overall charge and/or viscosity balance; and 3) an imaging component. The polymers may include either natural or artificial, for example, albumins, silk, wool, chitosan, alginate, pectin, DNA, cellulose, polysialic acids, dendritic polylysine, poly (lactic-co-glycolic) acid (PLGA), gellan, polysaccharides and poly-aspartic acid, and combinations thereof. The ionic component may include, $M^+X^-$ or $M^{2+}Y^{2-}$ (as a generalized formula $M^{n+}Y^{n-}$), where M belongs to alkaline or alkaline earth metal such as Li, Na, K, Rb, Cs and X represents halides, acetate, and other equivalent counter balance to $M^+$, and Y can be $X_2$ or mixed halides, acetates, carbonate, sulfate, phosphate and other equivalent counter balance to $M^{2+}$ as well as formic acid, glycolic acid, lactic acid, propionic acid, caproic acid, oxalic acid, malic acid, citric acid, benzoic acid, uric acid and their corresponding conjugate bases. Other organic components can independently be substituted as described in Wang, S. et al, Mol. Pharmaceutics 2015, 12, 4478-4487.

For CT imaging, cesium, tantalum, iopamidol, iohexol, ioxilan, iopromide, iodixanol, ioxaglate, diatrizoate, metrizoate, iothalamate, ethiodized polymers such as PLGA, PEG, albumins, DNA, RNA, ionic poly-carbohydrates and the combinations there of can be utilized; For ultrasound imaging, polymers are in general hypoechoic. However, when PLGA-PEG-PLGA (a block co-polymer, a reverse phase-transition hydrogel) is used, the polymer appears hypoechoic immediately after injection but subsequently turns into hyperechoic as temperature increases, indicating likely imageability. A similar observation was made when albumin is used as a carrier polymer.

Upon application of the electromagnetic energy (e.g., microwave, RF, electroporation), remotely deposited TA can absorb the energy much more effectively than the surroundings and help extend the ablation zone. Here, "remotely deposited TA" means in the far range, so would mean distance greater or equal to 1.5 cm from the microwave antenna, for example, when the conditions (e.g., 60 W 915 MHz for 10 minutes) are used. Using TA, the ablation zone can extend further from the antenna for a given power/time treatment, or the same ablation volume can be effectively ablated in a shorter time, or the degree of heating can be enhanced in specific tissue regions that are inherently less capable of microwave heating.

Upon application of the electromagnetic treatment energy (e.g., microwave, RF, electroporation) TA deposited adjacent to a large blood vessel can protect the ablation zone from heat loss, therefore TA can mitigate the "heat sink" effect to assure complete ablation. Moreover, suitably-placed TA may extend ablation to the far side of a vessel, enabling new treatment geometries for simple microwave antennas.

In addition, TA can be used in embolization/ablation combination treatments to destroy tumors. TA may be formulated with a similar viscosity to Lipiodol, and thus can be delivered via an intravascular catheter to be deposited accurately. A subsequent ablation can destroy tumors effectively.

The TA formulation may include excipients, which may depend upon the specific purpose. Excipients may, for example, include, PEG, lactose, microcrystalline cellulose, sodium starch glycolate, croscarmellose sodium, PVP, HPMC, magnesium stearate, colloidal $SiO_2$.

The tissue targets may be quite diverse, and use of TA in the field of Cancer/Tumor ablation may include breast (benign and malignant, thyroid (benign and malignant), lung (primary and metastatic), liver (primary and metastatic, liver surgery margin coagulation), adrenal (benign functioning, caner and metastatic), kidney (primary and metastatic), bone, prostate, soft tissue (primary and metastatic). In addition, the enhanced ablation accuracy, speed and uniformity offer promising improvements for Endometrial ablation/Menorrhagia: Uterus; Spinal Decompression and Denervation; Benign Prostatic Hyperplasia (BPH); as well as treating other tissues such as Esophagus (reflux), bronchial tree (emphysema reduction), biliary tree (stent obstruction from tumor), joints (laxity), surgical resection and bleeding.

The invention being thus described, further variations, modifications and examples thereof will be understood by one of ordinary skill in the art and all such variations and modifications are deemed to be within the scope of the invention described and claimed herein.

The invention claimed is:

1. A method of tissue ablation using one or more electrode or microwave antennae positioned and operated to ablate a tissue target in a subject, the method comprising:
   placing a thermal accelerant to enhance the degree or extent of ablation to the target, the thermal accelerant comprising: (i) a carrier; (ii) an ionic component; and (iii) an imaging component, wherein the carrier includes an active component that, when heated, produces heat onto the tissue target in the subject.

2. The method of claim 1, wherein the thermal accelerant includes a material having a dipole moment in a range of approximately 10.4 to approximately 710.

3. The method of claim 2, wherein the thermal accelerant is positioned to enhance heating by applied electromagnetic energy in a far field, peripheral or drop-off region or region of tissue variation to thereby extend ablation effects to said region.

4. The method of claim 2, wherein the thermal accelerant is positioned between an ablation site and a heat sink, such as a blood vessel, to modulate conduction of heat away from the ablation site and/or isolate the heat sink from the ablation site and thereby enable faster or more uniform heating of a region including the intended ablation site.

5. The method of claim 2, wherein the thermal accelerant is positioned as a microwave shield between an ablation site and healthy tissue to protect the healthy tissue from ablation damage by microwaves.

6. The method of claim 2, wherein the thermal accelerant is positioned as a thermal enhancer at a site distal to a sensitive or healthy proximal tissue to selectively ablate the distal site while applying a lower dose of RF or microwave radiation proximally and thereby protect the healthy tissue from ablation damage.

7. The method of claim 1, wherein the thermal accelerant includes cesium chloride or other ionic component in an amount or concentration for effectively absorbing microwave energy for local hyperthermic tissue ablation and is imaged via MRI medical imaging equipment set to enhance display of differences in signal decay with respect to surrounding tissue.

8. The method of claim 1, wherein the thermal accelerant:
   (a) enhances the heating by applied electromagnetic energy in a far field, peripheral or drop-off region or region of tissue variation to thereby extending the ablation effects;
   (b) is visible under various imaging modalities; and
   (c) is injectable.

9. The method of claim 8, wherein the thermal accelerant essentially remains in the area of application.

10. The method of claim 8, wherein the thermal accelerant is non-toxic.

11. The method of claim 1, wherein
   (i) the carrier is a polymer or a polymeric material selected from the group consisting of: albumin, alginate, cellulose, chitosan, dendritic polylysine, DNA, gellan, pectin, poly-aspartic acid, polyethylene glycol covalently esterified by a poly lactic-co-glycolic acid on both ends (PLGA-PEG-PLGA), poly(lactic-co-glycolic) acid (PLGA), polysaccharides, polysialic acids, silk, and wool, and a combination thereof;
   (ii) the ionic component is selected from the group consisting of: $M^{n+}X^{n-}$, wherein M is a cation and is selected from the group consisting of an alkaline or alkaline earth metal selected from barium, beryllium, calcium, cesium, francium, magnesium, potassium, radium, rubidium, sodium, and strontium; X is an anion and is selected from acetate, carbonate, halide, phosphate, and sulphate; n+ represents 1, 2, 3, or 4; n− represents 1, 2, 3, or 4; and
   (iii) the imaging component is selected from the group consisting of: cesium, diatrizoate, iodixanol, iohexol, ionic poly-carbohydrates, iopamidol, iopromide, iothalamate, ioxaglate, ioxilan, metrizoate, PLGA, PEG, RNA, tantalum, and a combination thereof.

12. The method of claim 1, wherein the ionic component is selected from the group consisting of: calcium chloride, cesium chloride, lithium chloride, potassium chloride, rubidium chloride, sodium chloride, and a combination thereof.

13. The method of claim 1, wherein the ionic component is selected from the group consisting of: benzoic acid, caproic acid, citric acid, formic acid, glycolic acid, lactic acid, malic acid, oxalic acid, propionic acid, uric acid and a corresponding conjugate base thereof.

14. The method of claim 1, wherein the ionic component is a chaotrope.

15. The method of claim 1, wherein a concentration of the carrier is in a range from approximately 200 mg/ml to approximately 500 mg/ml.

16. A method of ablating a tumor tissue target in a subject, the method comprising:
   positioning a) one or more electrodes and/or b) one or more microwave antennae relative to the tissue target;
   positioning a thermal accelerant in vivo in the subject relative to the tissue target, the thermal accelerant comprising (1) a carrier, (ii) an ionic component, and (iii) an imaging component,
   energizing the a) one or more electrodes and/or b) one or more microwave antennae to produce an energy to heat and ablate the tissue target and to heat the thermal accelerant,
   the energy from energizing the a) one or more electrodes and/or b) one or more microwave antennae heating the carrier to at least in part ablate the tissue target.

17. The method of claim 16 wherein energizing comprises applying microwave energy to the one or more microwave antennae.

18. The method of claim 16 wherein energizing comprises applying RF energy to the one or more electrodes.

19. The method of claim 16 where the thermal accelerant includes a high dipole moment material operable to convert the energy to a thermal energy, the high dipole moment having a range from approximately 10.4 to approximately 710.

20. The method of claim 16, wherein a concentration of the carrier is in a range from approximately 200 mg/ml to approximately 500 mg/ml.

21. The method of claim 16 wherein the carrier is heated to a temperature at which protein denaturation occurs.

22. The method of claim 16 wherein the carrier is heated to a temperature of 60° C. or greater.

* * * * *

UNITED STATES PATENT AND TRADEMARK OFFICE
CERTIFICATE OF CORRECTION

PATENT NO. : 10,722,289 B2
APPLICATION NO. : 15/389809
DATED : July 28, 2020
INVENTOR(S) : William Keun Chan Park It is certified that error appears in the above-identified patent and that said Letters Patent is hereby corrected as shown below:

In the Claims

At Column 18, Claim number 16, Line number 38, please replace "(1)" with -- (i) --

Signed and Sealed this
Eighth Day of September, 2020

Andrei Iancu
*Director of the United States Patent and Trademark Office*